United States Patent
Liao et al.

(10) Patent No.: US 10,576,082 B2
(45) Date of Patent: Mar. 3, 2020

(54) ERBB2 REGULATES AUTOPHAGIC FLUX TO MODULATE THE PROTEOSTASIS OF APP-CTFS IN ALZHEIMER'S DISEASE

(71) Applicant: Academia Sinica, Taipei (TW)

(72) Inventors: Yung-Feng Liao, Taipei (TW); Bo-Jeng Wang, Kaohsiung (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 16/329,070

(22) PCT Filed: Sep. 3, 2017

(86) PCT No.: PCT/US2017/049992
§ 371 (c)(1),
(2) Date: Feb. 27, 2019

(87) PCT Pub. No.: WO2018/048755
PCT Pub. Date: Mar. 15, 2018

(65) Prior Publication Data
US 2019/0209565 A1 Jul. 11, 2019

Related U.S. Application Data

(60) Provisional application No. 62/384,172, filed on Sep. 6, 2016.

(51) Int. Cl.
| | | |
|---|---|---|
| *A61K 48/00* | (2006.01) | |
| *C07H 21/02* | (2006.01) | |
| *C07H 21/04* | (2006.01) | |
| *A61K 31/517* | (2006.01) | |
| *A61P 25/28* | (2006.01) | |
| *C12N 15/113* | (2010.01) | |
| *A61P 25/00* | (2006.01) | |

(52) U.S. Cl.
CPC ........... *A61K 31/517* (2013.01); *A61P 25/00* (2018.01); *A61P 25/28* (2018.01); *C12N 15/113* (2013.01); *C12N 15/1138* (2013.01); *C12N 2310/122* (2013.01); *C12N 2310/14* (2013.01); *C12N 2310/531* (2013.01); *C12N 2740/16043* (2013.01)

(58) Field of Classification Search
CPC .................... A61K 31/713; C12N 15/113
See application file for complete search history.

(56) References Cited

U.S. PATENT DOCUMENTS

| 9,271,987 B2 | 3/2016 | Zhong et al. |
| 2003/0171278 A1 | 9/2003 | Dennis |
| 2013/0302337 A1 | 11/2013 | Zhong et al. |
| 2015/0315244 A1* | 11/2015 | ElShamy ............. A61K 31/713 424/649 |

OTHER PUBLICATIONS

Long et al. (Disease Markers, May 2016, Article ID 4250480, pp. 1-9).*
Ryu et al. (Cell Death and Disease, Feb. 2016, 7, e2117).*
Zhang et al. (Pigment Cell Melanoma Res, May 2013;26(3):408-14).*
International Search Report for PCT/US2017/049992, dated Jun. 11, 2017.
Written Opinion of International Search Authority for PCT/US2017/049992, dated Jun. 11, 2017.
Jie Han et al. "Interaction between Her2 and Beclin-1 Proteins Underlies a New Mechanism of Reciprocal Regulation" J Biol Chem. Jul. 12, 2013; 288(28): 20315-20325.
Rama Krishna Kancha et al. "Differential Sensitivity of ERBB2 Kinase Domain Mutations towards Lapatinib" PLoS ONE 6(10): e26760. doi: 10.1371/journal.pone.0026760.
Wong YC et al. "Autophagosome dynamics in neurodegeneration at a glance" J Cell Sci. Apr. 1, 2015;128(7):1259-67.

* cited by examiner

*Primary Examiner* — Amy H Bowman
(74) *Attorney, Agent, or Firm* — Hsiu-Ming Saunders; Intellectual Property Connections, Inc.

(57) ABSTRACT

Use of an ErbB2 inhibitor for promoting ErbB2-regulated autophagic degradation or clearance of APP-C99 and APP intracellular domain (AICD) and/or alleviating production of Abeta 40 and Abeta 42 in a subject in need thereof is disclosed. Use of an ErbB2 inhibitor for rescuing ErbB2-mediated inhibition of autophagic flux in a subject in need thereof is also disclosed. Use of an ErbB2 inhibitor for enhancing spatial learning and memory, and/or for cognitive improvement, in a subject with ErbB2-associated Alzheimer's disease is further disclosed. Also disclosed is use of an ErbB2 inhibitor for reducing intracellular levels of C99 and AICD without affecting extracellular domain-truncated Notch and Notch intracellular domain in a subject in need thereof.

12 Claims, 7 Drawing Sheets

Specification includes a Sequence Listing.

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: shRNA target sequence shControl_a

<400> SEQUENCE: 1
tgttcgcatt atccgaacca t                                              21

<210> SEQ ID NO 2
<211> LENGTH: 21
<212> TYPE: DNA
<213> ORGANISM: Artificial Sequence
<220> FEATURE:
<223> OTHER INFORMATION: shRNA target sequence shControl_b

<400> SEQUENCE: 2
cgaccacgca aatcagcgat t                                              21

<210> SEQ ID NO 3
<211> LENGTH: 21
<212> TYPE: DNA
<213> ORGANISM: Artificial Sequence
<220> FEATURE:
<223> OTHER INFORMATION: shRNA target sequence shErbB1_a

<400> SEQUENCE: 3
gctggatgat agacgcagat a                                              21

<210> SEQ ID NO 4
<211> LENGTH: 21
<212> TYPE: DNA
<213> ORGANISM: Artificial Sequence
<220> FEATURE:
<223> OTHER INFORMATION: shRNA target sequence shErbB1_b

<400> SEQUENCE: 4
gccacaaagc agtgaattta t                                              21

<210> SEQ ID NO 5
<211> LENGTH: 21
<212> TYPE: DNA
<213> ORGANISM: Artificial Sequence
<220> FEATURE:
<223> OTHER INFORMATION: shRNA target sequence shErbB2_a

<400> SEQUENCE: 5
gccatcaaag tgttgaggga a                                              21

<210> SEQ ID NO 6
<211> LENGTH: 21
<212> TYPE: DNA
<213> ORGANISM: Artificial Sequence
<220> FEATURE:
<223> OTHER INFORMATION: shRNA target sequence shErbB2_b

<400> SEQUENCE: 6
tgtggcctgt gcccactata a                                              21

<210> SEQ ID NO 7
<211> LENGTH: 4889
<212> TYPE: DNA
<213> ORGANISM: Homo sapiens

<400> SEQUENCE: 7

```
aagttcctgt gttctttatt ctactctccg ctgaagtcca cacagtttaa attaaagttc      60
ccggattttt gtgggcgcct gccccgcccc tcgtccccct gctgtgtcca tatatcgagg     120
cgatagggtt aagggaaggc ggacgcctga tgggttaatg agcaaactga agtgttttcc     180
atgatctttt ttgagtcgca attgaagtac cacctcccga gggtgattgc ttccccatgc     240
ggggtagaac ctttgctgtc ctgttcacca ctctacctcc agcacagaat ttggcttatg     300
cctactcaat gtgaagatga tgaggatgaa aacctttgtg atgatccact tccacttaat     360
gaatggtggc aaagcaaagc tatattcaag accacatgca aagctactcc ctgagcaaag     420
agtcacagat aaaacggggg caccagtaga atggccagga caaacgcagt gcagcacaga     480
gactcagacc ctggcagcca tgcctgcgca ggcagtgatg agagtgacat gtactgttgt     540
ggacatgcac aaaagtgagt gtgcaccggc acagacatga agctgcggct ccctgccagt     600
cccgagaccc acctggacat gctccgccac ctctaccagg gctgccaggt ggtgcaggga     660
aacctggaac tcacctacct gcccaccaat gccagcctgt ccttcctgca ggatatccag     720
gaggtgcagg gctacgtgct catcgctcac aaccaagtga ggcaggtccc actgcagagg     780
ctgcggattg tgcgaggcac ccagctcttt gaggacaact atgccctggc cgtgctagac     840
aatggagacc cgctgaacaa taccaccccct gtcacagggg cctccccagg aggcctgcgg     900
gagctgcagc ttcgaagcct cacagagatc ttgaaaggag gggtcttgat ccagcggaac     960
ccccagctct gctaccagga cacgattttg tggaaggaca tcttccacaa gaacaaccag    1020
ctggctctca cactgataga caccaaccgc tctcgggcct gccaccctg ttctccgatg     1080
tgtaagggct cccgctgctg gggagagagt tctgaggatt gtcagagcct gacgcgcact    1140
gtctgtgccg gtgctgtgc ccgctgcaag gggccactgc ccactgactg ctgccatgag    1200
cagtgtgctg ccggctgcac gggccccaag cactctgact gcctggcctg cctccacttc    1260
aaccacagtg gcatcgtgta gctgcactgc ccagccctgg tcacctacaa cacagacacg    1320
tttgagtcca tgcccaatcc cgagggccgg tatacattcg gcgccagctg tgtgactgcc    1380
tgtcccctaca actaccttc tacgacgtg ggatcctgca ccctcgtctg ccccctgcac    1440
aaccaagagg tgacagcaga ggatggaaca cagcggtgtg agaagtgcag caagccctgt    1500
gcccgagtgt gctatggtct gggcatggag cacttgcgag aggtgagggc agttaccagt    1560
gccaatatcc aggagtttgc tggctgcaag aagatctttg ggagcctggc atttctgccg    1620
gagagctttg atggggaccc agcctccaac actgccccgc tccagccaga gcagctccaa    1680
gtgtttgaga ctctggaaga gatcacaggt tacctataca tctcagcatg gccggacagc    1740
ctgcctgacc tcagcgtctt ccagaacctg caagtaatcc ggggacgaat tctgcacaat    1800
ggcgcctact cgctgacccct gcaagggctg gcatcagct ggctgggggct gcgctcactg    1860
agggaactgg gcagtggact ggccctcatc accataaca cccacctctg cttcgtgcac    1920
acggtgccct gggaccagct ctttcggaac ccgcaccaag tctgctcca cactgccaac    1980
cggccagagg acgagtgtgt gggcgagggc ctggcctgcc accagctgtg cgcccgaggg    2040
cactgctggg gtccagggcc cacccagtgt gtcaactgca gccagttcct tcggggccag    2100
gagtgcgtgg aggaatgccg agtactgcag gggctcccca gggagtatgt gaatgccagg    2160
cactgtttgc cgtgccaccc tgagtgtcag ccccagaatg gctcagtgac ctgttttgga    2220
ccggaggctg accagtgtgt ggcctgtgcc cactataagg accctccctt ctgcgtggcc    2280
cgctgcccca gcggtgtgaa acctgacctc tcctacatgc ccatctggaa gtttccagat    2340
```

-continued

```
gaggagggcg catgccagcc ttgccccatc aactgcaccc actcctgtgt ggacctggat    2400
gacaagggct gccccgccga gcagagagcc agccctctga cgtccatcat ctctgcggtg    2460
gttggcattc tgctggtcgt ggtcttgggg gtggtctttg ggatcctcat caagcgacgg    2520
cagcagaaga tccggaagta cacgatgcgg agactgctgc aggaaacgga gctggtggag    2580
ccgctgacac ctagcggagc gatgcccaac caggcgcaga tgcggatcct gaaagagacg    2640
gagctgagga aggtgaaggt gcttggatct ggcgcttttg gcacagtcta caagggcatc    2700
tggatccctg atggggagaa tgtgaaaatt ccagtggcca tcaaagtgtt gagggaaaac    2760
acatccccca aagccaacaa agaaatctta gacgaagcat acgtgatggc tggtgtgggc    2820
tccccatatg tctcccgcct tctgggcatc tgcctgacat ccacggtgca gctggtgaca    2880
cagcttatgc cctatggctg cctcttagac catgtccggg aaaaccgcgg acgcctgggc    2940
tcccaggacc tgctgaactg gtgtatgcag attgccaagg ggatgagcta cctggaggat    3000
gtgcggctcg tacacaggga cttggccgct cggaacgtgc tggtcaagag tcccaaccat    3060
gtcaaaatta cagacttcgg gctggctcgg ctgctgacca ttgacgagac agagtaccat    3120
gcagatgggg gcaaggtgcc catcaagtgg atggcgctgg agtccattct ccgccggcgg    3180
ttcacccacc agagtgatgt gtggagttat ggtgtgactg tgtgggagct gatgactttt    3240
ggggccaaac cttacgatgg gatcccagcc cgggagatcc ctgacctgct ggaaaagggg    3300
gagcggctgc cccagccccc catctgcacc attgatgtct acatgatcat ggtcaaatgt    3360
tggatgattg actctgaatg tcggccaaga ttccgggagt tggtgtctga attctcccgc    3420
atggccaggg accccagcg ctttgtggtc atccagaatg aggacttggg cccagccagt    3480
cccttggaca gcaccttcta ccgctcactg ctggaggacg atgacatggg ggacctggtg    3540
gatgctgagg agtatctggt accccagcag ggcttcttct gtccagaccc tgccccgggc    3600
gctgggggca tggtccacca caggcaccgc agctcatcta ccaggagtgg cggtggggac    3660
ctgacactag gctggagcc tctgaagag gaggccccca ggtctccact ggcaccctcc    3720
gaaggggctg gctccgatgt atttgatggt gacctgggaa tggggcagc caaggggctg    3780
caaagcctcc ccacacatga ccccagccct ctacagcggt acagtgagga ccccacagta    3840
cccctgccct ctgagactga tggctacgtt gccccctga cctgcagccc ccagcctgaa    3900
tatgtgaacc agccagatgt tcggcccag ccccttcgc cccgagaggg ccctctgcct    3960
gctgcccgac ctgctggtgc cactctggaa aggcccaaga ctctctcccc agggaagaat    4020
ggggtcgtca agacgttttt tgcctttggg ggtgccgtgg agaaccccga gtacttgaca    4080
ccccagggag gagctgcccc tcagccccac cctcctcctg ccttcagccc agccttcgac    4140
aacctctatt actgggacca ggacccacca gagcgggggg ctccacccag caccttcaaa    4200
gggacaccta cggcagagaa cccagagtac ctgggtctgg acgtgccagt gtgaaccaga    4260
aggccaagtc cgcagaagcc ctgatgtgtc ctcaggagc agggaaggcc tgacttctgc    4320
tggcatcaag aggtgggagg gccctccgac cacttccagg ggaacctgcc atgccaggaa    4380
cctgtcctaa ggaaccttcc ttcctgcttg agttcccaga tggctggaag gggtccagcc    4440
tcgttggaag aggaacagca ctggggagtc tttgtggatt ctgaggccct gcccaatgag    4500
actctagggt ccagtggatg ccacagccca gcttggccct ttccttccag atcctgggta    4560
ctgaaagcct tagggaagct ggcctgagag gggaagcggc cctaagggag tgtctaagaa    4620
caaaagcgac ccattcagag actgtccctg aaacctagta ctgcccccca tgaggaagga    4680
acagcaatgg tgtcagtatc caggctttgt acagagtgct tttctgttta gttttttactt    4740
```

```
tttttgtttt gtttttttaa agatgaaata aagacccagg gggagaatgg gtgttgtatg    4800
gggaggcaag tgtgggggt ccttctccac acccactttg tccatttgca aatatatttt    4860
ggaaaacagc taaaaaaaaa aaaaaaaaa                                      4889
```

ERBB2 REGULATES AUTOPHAGIC FLUX TO MODULATE THE PROTEOSTASIS OF APP-CTFS IN ALZHEIMER'S DISEASE

REFERENCE TO RELATED APPLICATION

This application is a national stage application (under 35 U.S.C. 371) of PCT/US2017/049992 filed on 3 Sep. 2017, which claims priority to U.S. provisional application 62/384,172 filed on 6 Sep. 2016, all of which are herein incorporated by reference in their entireties.

FIELD OF THE INVENTION

The present invention relates generally to Alzheimer's disease, more specifically to ErbB2 inhibitors for use in promoting autophagic clearance of amyloid precursor protein and treating Alzheimer's disease.

BACKGROUND OF THE INVENTION

Amyloid plaques, which cause neurodegeneration in the brains of Alzheimer's disease (AD) patients, are composed of amyloid-β (A β) peptides produced from cleavages of amyloid precursor protein (APP) by β- and γ-secretase. Therapeutic approaches to treating AD in the past decade have centered on the prevention of Aβ production, such as augmentation of β-secretase activity to reduce production of A β, or inhibition of β-γ-secretase activities. Unfortunately, the non-selective inhibition of β- and γ-secretases results in unavoidable side elects due to interference with other physiological substrates of β- and γ-secretases.

ErbB2 is tightly associated with neuritic plaques in AD. Autophagy controls the clearance of misfolded proteins and damaged organelles, and plays an essential role in maintaining neuronal functions. Whether farther ErbB2 inhibition could increase autophagic flux remains elusive.

SUMMARY OF THE INVENTION

In one aspect, the invention relates to use of an ErbB2 inhibitor in the manufacture of a medicament for promoting ErbB2-regulated autophagic degradation or clearance of amyloid precursor protein (APP) C-terminal fragment (APP-C99) and APP intracellular domain (AICD), and/or alleviating production of Aβ40 and Aβ42 in a subject in need thereof. The invention also relates to use of an ErbB2 inhibitor in the manufacture of a medicament for rescuing ErbB2-mediated inhibition of autophagic flux, and/or restoring the formation of Beclin-1-Vps34-Vps15 autophagy initiation complex in a subject in need thereof. The invention further relates to use of an ErbB2 inhibitor in the manufacture of a medicament for enhancing spatial learning and memory, and/or for cognitive improvement, in a subject with ErbB2-associated Alzheimer's disease. The invention additionally relates to use of an ErbB2 inhibitor in the manufacture of a medicament for reducing intracellular levels of C99 and AICD without affecting extracellular domain-truncated Notch (NΔE) and Notch intracellular domain (NICD) in a subject in need thereof.

In one embodiment, the subject exhibits one of the following characteristics: (i) loss of memory; (ii) loss of spatial memory and learning ability; and (iii) over-expression and/or a high level of ErbB2 in the hippocampus of the brain. In another embodiment, the subject is afflicted with sporadic Alzheimer's disease or Aβ-induced neurotoxicities. In one embodiment, the subject is a mammal.

In another embodiment, the ErbB2 inhibitor is selected from the group consisting of CL-387785, ErbB2-targeting short hairpin RNAs (shRNAs), and ErbB2-targeting small interfering RNAs (siRNAs). In another embodiment, the ErbB2 inhibitor exhibits one of the following characteristics: (i) having a specific binding affinity to ErbB2 monomer and having no effect on γ-secretase activity; and (2) having no effect on extracellular domain-truncated Notch, Notch intracellular domain levels, and Notch signaling.

In another embodiment, the medicament is formulated for a dosing regimen of once daily for more than 2 weeks, such as at least 15, 16, 17, 18, 19, 20 days or more. In another embodiment, the medicament is formulated for a dosing regimen of once daily for no less than 3 weeks. In another embodiment, the medicament is formulated for a dosing regimen of once daily at a human equivalent dose of about 5 mg/Kg×(0.040 Kg/weight of human in Kg)$^{0.33}$ or more.

In another embodiment, the autophagic degradation or clearance is EGFR/ErbB1-independent and/or accompanies a reduction in sequestosome 1/p62.

The invention also relates to an ErbB2 inhibitor for use in promoting ErbB2-regulated autophagic degradation or clearance of amyloid precursor protein (APP) C-terminal fragment (APP-C99) and APP intracellular domain (AICD), and/or alleviating production of Aβ40 and Aβ42 in a subject in need thereof. The invention further relates to an ErbB2 inhibitor for use in rescuing ErbB2-mediated inhibition of autophagic flux, and/or restoring the formation of Beclin-1-Vps34-Vps15 autophagy initiation complex in a subject in need thereof. The invention additionally relates to an ErbB2 inhibitor for use in enhancing spatial learning and memory, and/or for cognitive improvement, in a subject with ErbB2-associated Alzheimer's disease.

Alternatively, the invention relates to a method for promoting ErbB2-regulated autophagic degradation or clearance of APP-C99 and AICD and/or alleviating production of Aβ40 and Aβ42, rescuing ErbB2-mediated inhibition of autophagic flux, improving or enhancing spatial learning and memory in a subject with ErbB2-associated Alzheimer's disease, and/or reducing intracellular levels of C99 and AICD without affecting NΔE and NICD in a subject in need thereof. The method comprises administering to the subject in need thereof a therapeutically effective amount of an ErbB2 inhibitor.

DETAILED DESCRIPTION OF THE INVENTION

Figure 1:
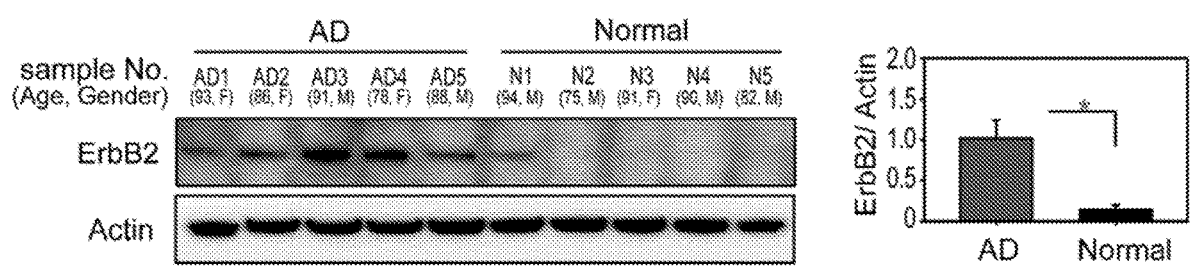
FIG. 1 shows that the levels of ErbB2 are positively correlated with age-related sporadic AD. Human hippocampal regions were analyzed by Western blotting with anti-EGFR(ErbB1), anti-ErbB2, and anti-actin antibodies. Data are shown as the mean±SD from three independent experiments, and were analyzed by Student's t-tests. * p<0.05.

As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Some terms used in this specification are more specifically defined below.

Definitions

The use of examples anywhere in this specification including examples of any terms discussed herein is illustrative only, and in no way limits the scope and meaning of the invention or of any exemplified term. Likewise, the invention is not limited to various embodiments given in this specification. Unless otherwise defined, all technical and scientific terms used herein have the same meaning as commonly understood by one of ordinary skill in the art to which this invention pertains. In the case of conflict, the present document, including definitions will control.

As used herein, "an ErbB2 inhibitor" is a compound or an agent that is effective in inhibiting ErB2 activity via either inhibiting ErbB2 phosphorylation (i.e., inhibiting ErbB2 activation, blocking ErbB2 kinase activity and downstream signaling) or causing a reduction in the ErbB2 protein level.

The term "treating" or "treatment" refers to administration of an effective amount of a therapeutic agent to a subject in need thereof, who has a disease, a symptom or predisposition toward such a disease, to cure, alleviate, relieve, remedy, ameliorate, or prevent the disease, the symptoms of it, or the predisposition towards it, or reduce incidence of symptoms. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on route of administration, excipient usage, and the possibility of co-usage with other therapeutic treatment.

The "Guidance for industry and Reviewers Estimating the Safe Starting Dose in Clinical Trials for Therapeutics in Adult Healthy Volunteers" published by the U.S. Department of Health and Human Services Food and Drug Administration discloses "a human equivalent dose" may be obtained by calculations from the following formula:

$$HED = \text{animal dose in mg/kg} \times (\text{animal weight in kg/human weight in kg})^{0.33}.$$

Abbreviations list. Aβ, amyloid-β; AD, Alzheimer's disease; APP, amyloid precursor protein; C99 (APP-CTF), 99-residue C-terminal fragment of APP; AICD, amyloid precursor protein intracellular domain; BRET, bioluminescence resonance energy transfer; PS, presenilins; PBS, phosphate-buffered saline; MVB, multi vesicular body; NICD, Notch intracellular domain; NΔE, extracellular domain truncated Notch; RAPT, N—[N-(3,5-difluorophenacetyl-L-alanyl)]-S-phenylglycine t-butyl ester; CL-387,785, N-[4-[(3-bromophenyl)amino]-6-quinazolinyl]-2-butynamide.

Proteolytic processing of amyloid precursor protein (APP) C-terminal fragments (APP-CTFs) by γ-secretase underlies the pathogenesis of Alzheimer's disease (AD). An RNAi screen using APP-CTF (C99)- and Notch-specific γ-secretase interaction assays identified an unique ErbB2-centered interaction network of 17 candidate modulators that was predicted to preferentially govern the proteostasis of APP-C99. Consistently, significantly elevated levels of ErbB2 were confirmed in the hippocampus of human AD brains. Overexpression of a kinase-dead monomeric form of ErbB2 effectively suppressed autophagic flux by interfering the interaction between Beclin-1 and the Vps34-Vps15 complex. Downregulation of ErbB2 by CL-387,785 decreased the levels of C99 and secreted Aβ in cellular, zebrafish, and mouse models of AD, through the activation of autophagy. Oral administration of an ErbB2-targeted CL-387,785 for 3 weeks significantly improves the cognitive functions of APP/PS1 transgenic mice. These findings were further corroborated by the concomitant increase in the levels of ErbB2 and reduction autophagy activity in human brains with sporadic AD. This work unveils a non-canonical function of the ErbB2 in modulating autophagy, establishing ErbB2 as a novel therapeutic target for AD.

We developed bioluminescence resonance energy transfer (BRET)-based cellular assays to systemically quantify the protein-protein interactions between γ-secretase and its substrates, either APP C-terminal fragment (APP-CTF; C99) or Notch extracellular domain truncation (NΔE), in response to the deficiency of a particular kinase or phosphatase encoded in human genome. This RNAi screen led us to identify an ErbB2-interacting network that plays a critical role in governing the substrate availability of γ-secretase.

The invention relates to the discovery that inhibition of ErbB2 expression can enhance C99 clearance, thereby effectively decreasing Aβ production through activating autophagy. The invention also relates to a ErbB2-targeted therapeutic strategy (e.g. CL-387,788), in contrast to pan-inhibition of γ-secretase, which could render cognitive improvement without eliciting complications associated with undesirable Notch inhibition for the next-generation treatment of AD.

EXAMPLES

Without intent to limit the scope of the invention, exemplary instruments, apparatus, methods and their related results according to the embodiments of the invention are given below. Note that titles or subtitles may be used in the examples for convenience of a reader, which in no way should limit the scope of the invention. Moreover, certain theories are proposed and disclosed herein; however, in no way they should limit the scope of the invention so long as the invention is practiced according to the invention without regard for any particular theory or scheme of action.

Materials and Methods

Study approval. The study was approved by the Institutional Review Board. Informed consent to share research tissue after death was obtained from all patients. The procedures for the animal study were approved by the Academia Sinica institutional Animal Care and Utilization Committee.

Statistics. Quantitative analysis of immunoblots was conducted with Image J (NIH) software, by determining the relative intensity of the immunoreactive bands after acquisition of the blot image with BIOSPECTRUM® 600 Imaging System (UVP). Statistical analyses were performed using two-way ANOVA. A value of $p \leq 0.05$ was considered significant.

Chemical reagents. Dimethyl sulfoxide (DMSO) was purchased from SIGMA-ALDRICH™. AG825 (an ErbB2 tyrosine kinase inhibitor), CL-387,785 (a dual ErbB1 and ErbB2 irreversible tyrosine kinase inhibitor), and N—[N-(3,5-difluorophenacetyl-L-alanyl)]-S-phenylglycine t-butyl ester (DAPT, a γ-secretase inhibitor) were purchased from EMD Millipore. Gefitinib (an ErbB1 tyrosine kinase inhibitor), and Lapatinib (a dual ErbB1 and ErbB2 tyrosine kinase inhibitor) were purchased from Selleckchem. All inhibitors were dissolved in DMSO to 10 mM and stored at −20° C. All other reagents were at least reagent grade and obtained from standard suppliers.

Plasmid construction. The cDNA sequences encoding, ErbB1, ErbB2, Beclin1, and LC3 were amplified from mRNA transcripts isolated from HEK293 cells by reverse transcription PCR. The cDNA sequence encoding *Renilla* luciferase (RL) was derived from pRL-TK (PROMEGA™). ECFP and EYFP were derived from pECFP-N1 and pEYTP-N1 (Clontech). C99 was constructed as previously described. An expression construct encoding a constitutively active membrane-bound Notch (NΔE), which acts as a direct substrate of γ-secretase independent of ligand binding, was a gift from Dr. Raphael Kopan (Washington University, St. Louis, Mo.). The cDNA expression plasmids encoding nicastrin (NCT) and presenilin 1 (PS1) were gifts kindly provided by Dr. Michael Wolfe (Brigham and Women's Hospital and Harvard Medical School, Boston, Mass.). RL-tagged PS1 was subcloned into pBudCE4.1 (Invitrogen). YFP-tagged NCT, C99, and NΔE were individually inserted into pcDNA5/TO (Invitrogen). The generation of Gal4/VP16-tagged C99 (C99-GV), Gal4/VP16-tagged NΔE (NΔE-GV), and Gal4-Luc has been described previously. The lentivectors for cDNA expression, including pLKO_AS2.puro, pLKO_AS2.zeo, and pLKO_AS3w.hyg were purchased from the National RNAi Core Facility Platform, Academia Sinica, Taipei, Taiwan. CFP-tagged C99 was inserted into pLKO_AS2.zeo between the Nhe I and Pme I sites under the control of the vector's CMV promoter. Another cDNA amplimer containing CMV promoter-driven YFP-tagged NΔE was then subcloned at the Mlu I site in the same vector to generate pAS2-CCNY, which enabled the co-expression of CFP-C99 and NΔE-YFP at the same efficiency in the same cells. Myc-his-tagged ErbB1, Myc-his-tagged ErbB2, YFP-tagged ErbB2 and YFP-tagged ErbB2ΔE (N-terminally 23-562 truncated ErbB2) were individually inserted into the pLKO_AS2.puro vector. Flag-tagged Beclin 1, CFP-tagged Beclin 1 and CFP-LC3 were individually inserted into pLKO_AS3w.hyg. Point-mutations of ErbB2 were constructed as described in a previous report and inserted into pLKO_AS2.puro.

Generation of stably transfected cell lines. T-REx 293 cells and culture-related reagents were purchased from Invitrogen. To generate BRET assays for the interactions between PS1 and a selective γ-secretase substrate (C99 or NΔE), HEK293 cells were transfected with RL-tagged PS1 using Lipofectamine 2000 Transfection Reagent (Invitrogen) according to the manufacturer's instructions. Transfected cells were cultured in DMEM growth media supplemented with 10% FBS and 250 μg/ml zeocin. Transfected and zeocin-resistant cells that constitutively express recombinant RL-PS1 (RL-PS1 cells) were then further transfected with an expression construct encoding YFP-tagged NCT, YFP-tagged C99, or YFP-tagged NΔE. The double-transfected cells were cultured in DMEM supplemented with 10% FBS, 250 μg/ml zeocin, and 200 μg/ml hygromycin B. Individual colonies of double-transfected cells resistant to zeocin and hygromycin were isolated. The optimal cell line exhibiting constitutive co-expression of RL-PS1 and YFP-NCT was selected and named PS1-NCT-BRET. The optimal cell line exhibiting constitutive co-expression of RL-PS1 and YFP-C99 was selected and named PS1-C99-BRET. Another line of double-transfected cells that stably coexpress RL-PS1 and YFP-NΔE was selected and named PS1-NΔE-BRET.

Cell-based, substrate-selective γ-secretase assays were generated by transfecting T-REx293 cells with a Gal4 promoter-driven luciferase reporter gene (Gal4-Luc), and then selecting with DMEM medium containing 10% FBS, 5 μg/ml blasticidin, and 250 μg/ml zeocin. The optimal stably transfected cell line (Gal4-Luc) was further transfected with either C99-GV or NΔE-GV, followed by selection with DMEM medium containing 10% FBS, 5 μg/ml blasticidin, 25 μg/ml zeocin, and 200 μg/ml hygromycin B. The optimal C99-specific cell line for the γ-secretase assay was that which exhibited the highest tetracycline-induced C99-dependent luciferase signal that was significantly suppressed by DAPT to the basal level (i.e., comparable to the signal obtained in the absence of tetracycline induction). The optimal NΔE-specific cell line for the γ-secretase assay was that which exhibited the highest tetracycline-induced NΔE-dependent luciferase signal. Based on these criteria, clones CG and NG were selected and optimized for the cell-based C99- and NΔE-specific γ-secretase assays, respectively.

To generate a cellular γ-secretase assay that could be used to simultaneously identify cleavage of C99 and NΔE and the production of AICD and NICD, we infected HEK293 cells with pAS2-CCNY and selected transfectants with DMEM medium containing 10% FBS and 250 μg/ml zeocin. The optimal cell line exhibited equivalent levels of CFP-C99 and YFP-NΔE, and cleavage of both were completely suppressed by DAPT. The CCNY clone was selected and optimized for the cell-based C99-NΔE dual γ-secretase assay.

CCNY cells were infected with ErbB1-HA for 24 h, followed by infection with ErbB2-myc-his to generate CCNY21 cells. The CCNY21 cells were maintained in DMEM medium containing 10% FBS, 250 μg/ml zeocin, 200 μg/ml hygromycin B, and 2 μg/ml puromycin. IMR32 cells (human neuroblastoma cell line) were infected with pAS2-CY and selected with DMEM medium containing 10% FBS and 50 μg/ml zeocin.

Preparation of shRNA-containing lentiviral stocks. The human kinase and phosphatase set of lentiviral shRNAs was purchased from the National RNAi Core Facility Platform, Academia Sinica. The target sequences of the shRNAs used were as follows: TGTTCGCATTATCCGAACCAT (shControl_a; SEQ ID NO: 1), CGACCACGCAAATCAGCGATT (shControl_b; SEQ ID NO: 2), GCTGGATGATA-GACGCAGATA (shErbB1_a; SEQ ID NO: 3), GCCA-CAAAGCAGTGAATTAT (shErbB1_b; SEQ ID NO: 4), GCCATCAAAGTGTTGAGGGAA (shErbB2_a; SEQ ID NO: 5), and TurocicCTOTGCCCAcTATAA (shErbB2_b; SEQ ID NO: 6). Lentivirus was produced as previously described using BES buffer containing calcium phosphate. Briefly, 293T cells at 30-40% confluence in T75 flasks were transfected with a DNA mix containing 7.5 μg package plasmids (pCMVΔR8.91 VSV-G/pMD2.G=3:1) and 7.5 μg targeting hairpin-pLKO.1 lentivector. The transfection mixture (50 μl 2.5 M $CaCl_2$, the DNA mix, and 500 μl 50 mM DES buffer pH 6.95, in a final volume of 1 ml) was added to the culture media, which was then incubated at 37° C. for 16 h. Transfected cells were incubated with 10 ml fresh DMEM growth medium containing 10 mM sodium butyrate. The conditioned media were harvested daily for 3 days, and detached cells were removed by centrifugation at 1000 g. Packaged lentiviral particles in clarified conditioned media were harvested by ultracentrifugation at 25,000 rpm for 3 h at 4° C. in a SW-28 rotor (Beckman Coulter). The viral harvests were resuspended in 1 ml fresh DMEM growth medium and stored at −80° C. The virus titers were determined using a cell-viability assay. HEK293 cells were seeded onto 96-well microplates (10,000 cells/well) with 100 μl DMEM growth medium, and cultured overnight. Lentiviral stocks at 2-fold serial dilutions were then added, and the cells were incubated at 37° C. for 24 h. Infected cells were treated with corresponding antibiotics (200 μg/ml hygromycin B, 250 μg/ml zeocin, or 2 μg/ml puromycin) at 37° C. for 48 h to select for infected cells. Cell viability was measured using the CellTiter 96 AQueous One Solution Cell Proliferation Assay (PROMEGA™), according to the manufacturer's instructions. One viral titer was defined as the viral concentration of the diluted viral stock that did not induce a significant reduction in cell viability compared to control cells, which were neither infected nor treated with antibiotic. ErbB2 DNA sequence is as listed in SEQ ID NO: 7, from which nucleotide 577 to nucleotide 4254 is the cDNA sequence.

Preparation of cell extracts. To prepare total cell-free extracts, we harvested cells in 6-well microplates with ice-cold PBS containing 20 mM EDTA, and then pelleted the cells by centrifugation. PBS-washed cells were resuspended in a lysis buffer containing 1% Triton X-100, 50 mM Tris-HCl pH 7.5, 150 mM NaCl, 25 mM β-glycerophosphate, 1 mM $Na_3VO_4$, and protease inhibitor cocktail set V (Merck). Following the removal of cell debris by centrifugation, clarified lysates were processed for immunoprecipitation, Western blotting, or quantification of BCA protein content.

Immunoprecipitation of ErbB2 and Beclin1 complex. Cells at 90% confluency in a 10 cm dish were harvested and lysed in 1 ml of immunoprecipitation buffer containing 1% CHAPSO, 25 mM HEPES pH 7.0, 150 mM NaCl, 25 mM β-glycerophosphate, 1 mM $Na_3VO_4$, 1 mM EDTA, and protease inhibitor cocktail set V. Clarified lysates containing equal amounts of protein were mixed with mouse anti-GFP (SIGMA-ALDRICH™) or anti-Flag (SIGMA-ALDRICH™)-conjugated Protein G Magnetic Beads (Millipore). The protein-bound beads were washed three times with immunoprecipitation buffer. Bound proteins on the washed beads were disassociated by the addition of 100 μl 2×SDS sample buffer, and subsequently analyzed by Western blotting.

Human brain sample preparation. Human hippocampal tissues (AD2-5 and N1-4) were provided by the Alzheimer's Disease Center, University of California Davis Medical Center (NIH AG10129). The study was approved by the Institutional Review Board. Informed consent to share research tissue after death was obtained from all patients. Two additional human hippocampal samples (GTX26445 with AD pathology and GTX28726 as a normal control), and three human whole brain lysates with different ages ere purchased from GeneTex Inc. Brain tissues were homogenized in RIPA buffer (25 mM Tris-HCl, pH 7.6, 150 mM NaCl, 1% NP-40, 1% sodium deoxycholate, and 0.1% SDS). Clarified lysates were analyzed by Western blotting.

Western blotting analysis. Protein concentration was measured with the BCA Protein Assay Kit (Pierce). Clarified cell extracts were mixed with 6×SDS sample buffer (350 mM Tris-HCl pH 6.8, 10% SDS, 30% glycerol, 10% dithiothreitol, and 0.1% bromophenol blue) and boiled at 100° C. for 5 min. Equal amounts of denatured proteins were resolved on 10% Tris-glycine polyacrylamide gels and transferred electrophoretically to BioTrace PVDF Transfer Membranes (Pall). The antibodies used for immunoblotting were as follows: mouse anti-Aβ1-16 (6E10, Covance), mouse anti-ErbB2 (Origene), rabbit anti-phosphoErbB1 (Tyr1068, BioLegend), rabbit anti-phosphoErbB2 (Tyr1278), rabbit anti-cleaved Notch1 ($Val^{1744}$) (Cell Signaling Technology), mouse anti-His Tag (Anogen), chicken anti-EbbB2, rabbit anti-Vps34 and rabbit anti-Vps15 (CeneTex), mouse anti-HA, mouse anti-GFP, mouse anti-Beclin 1, rabbit anti-GAPDH, HRP-conjugated anti-mouse IgG, and HRP anti-rabbit IgG (Santa Cruz). The blot image was acquired using BioSpectrum 600 (UVP). Quantitative analyses of blot images were processed using Image J software (NIH) to determine the relative densities of immunoreactive bands.

BRET measurement and quantification. PS1-NCT-BRET, PS1-C99-BRET, and PS1-NΔE-BRET cells (10,000 cells/well) were seeded onto 96-well microplates (Costar) overnight. Cells were infected with the indicated shRNAs (human kinase and phosphate set from the RNAi Core at Academia Sinica) at 37° C. for 48 h. Cellular BRET signals were determined by the addition of coelenterazine, the substrate of *Renilla* luciferase, to a final concentration of 0.35 μM. The RL-emitted luminescence and YFP-emitted fluorescence were simultaneously quantified by a luminescence/fluorescence plate reader (VICTOR Light, PerkinElmer). The BRET signals were quantified as in previous studies, and the BRET Index (leaked emission from RL at YFP channel/total emission by RL) was determined by using cells stably overexpressing RL-PS1. The formula for determining the BRET signal was as follows: BRET signal=[YFP fluorescence−(*Renilla* luciferase luminescence×BRET $Index^{RL-PS1}$)]/*Renilla* luciferase luminescence.

The BRET signal of each well of the microplate was totaled and averaged, and the mean BRET signal of each microplate was taken as 100% control BRET. Candidate genes whose shRNAs induced a larger change in PS1-C99-BRET cells than in PS1-NΔE-BRET cells ($BRET^{PS1-C99}/BRET^{PS1-N\Delta E}<0.7$) were selected and further analyzed using STRING 9.0.

Cell-based γ-secretase assays for the nuclear function of AICD or NICD. NG or CG cells (20,000 cells/well) were plated onto 96-well microplates and treated with the indicated compounds or cytokines in the presence of 1 μg/ml tetracycline for 24 h. To examine the effect of RNAi-mediated knockdown, we seeded CG or NG cells onto 96-well microplates, infected them with the indicated lentiviral shRNAs for 48 h, and then incubated them in the presence of tetracycline at a final concentration of 1 μg/ml for 24 h. Cellular luminescence was determined by the addition of Steady-Glo Luciferase Assay reagents (PROMEGA™), according to the manufacturer's instructions. Aβ ELISA. HEK293 cells (CCNY21) that coexpress CFP-C99, YFP-NE, ErbB1, and ErbB2 or IMP32 cells that overexpress YFP-C99 were infected with lentiviral shRNAs as specified and cultured at 37° C. for 48 h, followed by replacement with fresh DMEM growth medium and additional incubation at 37° C. for 24 h. To determine EGF- and inhibitor-elicited effects on Aβ production, we treated CCNY21 cells at a confluence of 50% with EGF (10 ng/ml) or ErbB inhibitors (1 μM) in DMEM growth medium at 37° C. for 24 it. Conditioned media were harvested and clarified by centrifugation. The level of secreted Aβ40 was quantified using a human Aβ40 sandwich ELISA kit (Invitrogen) according to the manufacturer's instructions.

Cross-linking of membrane protein. CHO-K1 cells expressing mock constructs, wtErbB2, or ErbB2-VVI/AAA (subconfluent in 6 well plates) were rinsed twice with PBS and treated with 1 mM BS3 (bis(sulfosuccinimidyl)suberate) in 1 ml PBS at RT for 2 h. Cells were harvested with ice-cold PBS containing 20 mM EDTA and washed with PBS twice. Clarified cell extracts were analyzed with Western blotting.

Figure 6:
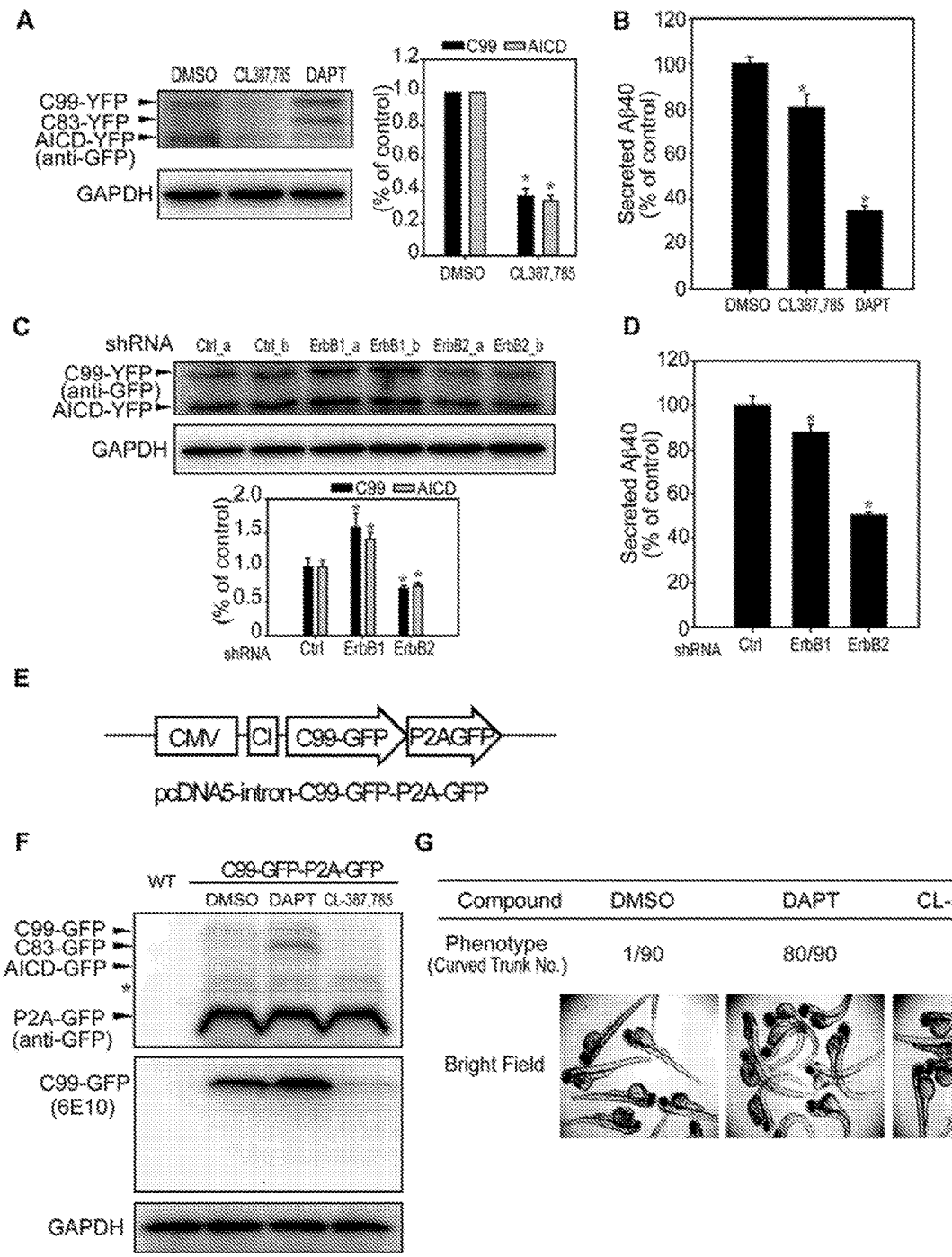
FIG. 6 shows that CL-387,785 or shErbB2 can effectively reduce the levels of C99, AICD, and secreted Aβ40 without perturbing Notch-dependent somite development in a zebralish model of amyloidopathy. (A) IMR32 cells overexpressing C99-YFP were grown with 2 ml fresh culture medium in 6-well plates, and treated with 1 μM CL-387,785 or DAPT at 37° C. for 24 h. The cell extracts were analyzed by Western blotting. (B) Conditional media were harvested and processed for determination of secreted Aβ40 using a colorimetric Aβ40-specific ELISA kit. (C) C99-YFP-expressing IMR32 cells (160,000 cells/well) were seeded onto 6-well plates and cultured at 37° C. for 24 h, and infected with ErbB1- or ErbB2-targeting shRNA lentivirus for an additional 48 h. Infection mixtures were replaced with 2 ml fresh culture medium, and infected cells were then incubated at 37° C. for an additional 24 h. The cell extracts were analyzed by Western blotting with anti-GFP antibody. (D) The conditioned media were harvested and processed for determination of secreted Aβ40. Data are the mean±SD from three independent experiments, and were analyzed by Student's t-tests. * p<0.05. (E) Schematic presentation of the DNA construct encoding recombinant C99-GFP-P2A-GFP. CMV, human cytomegalovirus promoter; CI, chimeric intron; P2A, porcine teschovirus 2A peptide. (F) Zebrafish embryos at the one-cell stage were injected with C99-GFP- P2A-GFP plasmid, and treated with the indicated compounds from 48 hpf to 72 hpf at 28° C. Clarified lysates derived from treated embryos were analyzed by Western blotting with anti-GFP (for C99, C83, AICD, and P2A-GFP plasmid injection control), anti-Aβ1-16 (6E10, for full-length C99), and anti-GAPDH. The asterisk indicates unidentified bands. (G) The phenotypes of C99-expressing zebrafish embryos treated with the indicated compounds were imaged by bright-field microscopy and fluorescence microscopy. The number of embryos exhibiting curved trunk at 72 hpf were recorded, n=90.

Overexpression of APP-C99 zebrafish. GFP-tagged APP-C99 was constructed in pcDNA5/TO as shown in FIG. 6E. To minimize the plasmid size, we removed the hygromycin resistance gene and tetracycline repressor binding site. The chimeric intron sequence was from pRL-TK. The P2A sequence was previously described, and used as an injection control. Each one-cell-stage zebrafish embryo was injected with approximately 200 pg of linearized pcDNA5-intron-C99-GFP-P2A-GFP plasmid. The injected zebrafish were maintained at 28° C. for 48 h, and then treated with the indicated chemical compounds for a further 24 h. Treated zebrafish embryos were sacrificed by immersion in ice-cold water. The protein samples were extracted using RIPA buffer, and sonicated briefly. Clarified lysates containing equal amounts of protein were analyzed by Western blotting.

Mouse strain and Morris water maze. B6C3-tag (APPswe.PSEN1dE9)85Dbo/MmJax] mice expressing mutant chimeric mouse/human amyloid precursor protein (Mo/HuAPP695swe) and a mutant human presenilin (PS1ΔE9) driven by prion protein promoter were purchased from The Jackson Laboratory. Male mice at 15 month old were given daily oral doses of 200 μl vehicle alone (100 μl DMSO in 5% 2-Hydroxypropyl-β-cyclodextrin, n=4 for both WT and transgenic mice), or 5 mg/kg CL387,785 (transgenic mice n=4) for 20 days. The average body weight of wild-type littermates is 35.86 g, the APPswe/PS1 Tg mice in DMSO-treated control group 37.48 g, and the Tg mice in CL387-795-treated group 40.39 g at day 0. Thus, the average body weight of AD transgenic mice used in the experiments was about 40 g. The Morris water maze test was performed. Pre-tests were performed on days 9 and 10 (each mouse for 60 sec) with a visible platform to let mice adapt to the environment. The escape latency (time taken to find the invisible platform; maximum time below 60 sec) was recorded from day 11 to day 20. The platform was removed on day 21 for the probe test, one day after the learning ability test. Mice were allowed to swim for 90 sec. The tracking video and time taken were recorded and analyzed using Noldus EthoVision XT software. Mice were sacrificed by isoflurane inhalation. Left brains were fixed with 4% formaldehyde in PBS. Right brains were homogenized and sonicated briefly for Western blotting and ELISA.

Results

An shRNA Screen Identified Candidate Genes that Differentially Regulate the Proteolysis of APP-C99 and NΔE Whether additional kinases or phosphatases could differentially modulate the interaction between APP-C99 and PS1 (the catalytic subunit of γ-secretase) without affecting the interaction between NΔE and PS1 was determined. Cell-based bioluminescence resonance energy transfer (BRET) assays to quantitatively measure the interactions between γ-secretase and its substrates were established and validated. BRET cell lines were subjected to RNAi screens with the Human Kinase and Phosphatase (KP) Subset, which contains 5667 validated shRNA-encoding lentiviral clones targeting 777 human kinases and 237 human phosphatases. If a targeted gene is involved in modulating PS1-C99 or PS1-NΔE interaction, its downregulation would reduce the BRET signal. By selecting those genes whose downregulation resulted in a ratio of PS1-C99-elicited BRET signal versus PS1-NΔE-elicited BRET signal lower than 70%, we identified candidate genes that preferentially influence the PS1-C99 interaction. Using STRING software at the highest stringency (0.9 confidence index), it was revealed that ErbB2 could potentially function as the master regulator of γ-secretase substrate selectivity.

The Expression Levels of ErbB2 are Significantly Elevated in AD Brains.

The levels of Erbβ2 in brain homogenates derived from either normal individuals or patients with sporadic AD were examined. Significantly higher levels of ErbB2 expression in hippocampal regions of AD patients were observed as compared to aged-matched normal controls, whereas the levels of EGFR exhibited no significant difference between AD brain and age-matched control brain (FIG. 1). The levels of ErbB2 in whole brain homogenates were significantly higher in newborn mice than in young (3-month-old) and old (15-month-old) mice. Consistently, the expression of ErbB2 in human brain was gradually decreased with increasing age. HEK293 cells that are co-transfected with YFP-tagged C99 and His-tagged ErbB2 exhibited a significant accumulation of C99 and AICD as compared to the mock-transfected cells. These results suggest that the recurring ErbB2 in aged brain could be a disease-driving instigator for sporadic AD.

Inhibition of ErbB2 by CL-387,785 can Differentially Promote the Clearance of C99 without Affecting Notch Signaling A HEK293-derived cell fine (CG) was stably co-transfected with a tetracycline-inducible C-terminally Gal4/VP16-tagged C99 and a Gal4 promoter-driven luciferase reporter gene. Another HEK293-derived cell line (NG) was stably co-transfected with a tetracycline-inducible C-terminally Gal4/VP16-tagged NΔE and Gal4 promoter-driven luciferase reporter gene. Both the CG and NG cell lines exhibited decreased γ-secretase-dependent luciferase signals in the presence of DAPT, a known γ-secretase inhibitor, in a dose-dependent manner, suggesting that γ-secretase in CG and NG cells exhibited comparable catalytic properties.

Figure 2:
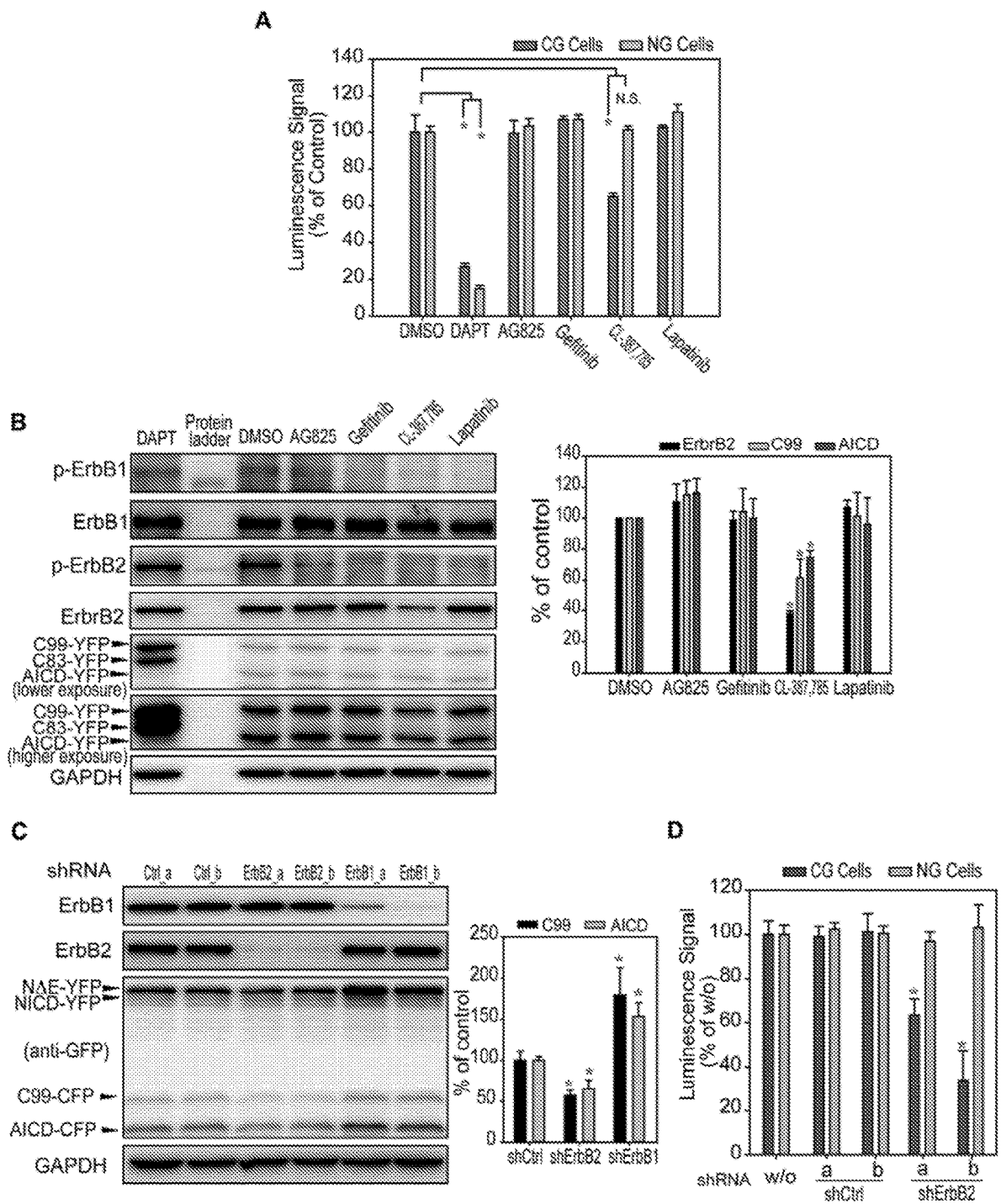
FIG. 2 shows that alterations in the levels of ErbB1 and ErbB2 can reciprocally govern the steady-state levels of C99/AICD and NΔE/NICD. (A) Adherent CG and NG cells (20,000 cells/well) were treated with 1 μM of the indicated ErbB1/2-selective tyrosine kinase inhibitors in the presence of 1 μg/ml tetracycline at 37° C. for 24 h. The luminescence signals emitted by cells treated with vehicle alone (Ctrl, 0.1% DMSO) were referred to as 100% relative luminescence signals. The luminescence signals generated by γ-secretase-mediated proteolysis of C99 (CG) or NΔE (NG) were determined using the Steady-Glo luciferase assay reagent. (B) HEK293 overexpressing C99-YFP cells were treated with 1 μM of the indicated ErbB1/2 tyrosine kinase inhibitors at 37° C. for 24 h. Clarified lysates were analyzed by Western blotting and quantified by Image J. (C) HEK293 overexpressing ErbB1 ErbB2, CFP-tagged C99, and YFP-tagged NΔE cells were infected with gene-targeting shRNA-encoding lentivirus (shErbB1 or shErbB2) at 37° C. for 48 h. Clarified lysates containing equivalent amounts of proteins were examined by Western blotting and quantified by Image J. (D) CG and NG cells were infected with gene-targeting shRNA-encoding lentivirus at 37° C. for 48 h. Following induction with 1 μg/ml tetracycline for 24 h. Cells infected with empty lentivirus (w/o) or LacZ-targeting shRNA lentivirus (shCtrl_a and shCtrl_b) were included as controls. Data are shown as the mean±SD from three independent experiments, and were analyzed by Student's t-tests. * p<0.05.

To determine whether ErbB1 or ErbB2 receptor tyrosine kinase activity is essential for the differential modulation of C99 cleavage, we first examined the luminescence signals in CG and NG cells treated with various ErbB1/2 inhibitors. Our data showed that only CL-387,785 (ErbB1/2 dual), but not AG825 (ErbB2-selective), Gefitinib (ErbB1-selective), nor Lapatinib (ErbB1/2 dual), effectively blocked the processing of C99 (in CG), but not NΔE (in NG) (FIG. 2A). Furthermore, using C99-YFP-overexpressing HEK293 cells, we found that treatments with CL-387,785 concomitantly decreased the levels of ErbB2, C99, and AICD (FIG. 2B).

To address how ErbB1 and ErbB2 could act in a differential mode upon the co-existence of C99 and NΔE, we generated a HEK293 cell line that stably co-expressed ErbB1, ErbB2, CFP-tagged C99, and YFP-tagged NΔE. Consistently, ErbB2 knockdown, but not ErbB1 knockdown, was sufficient to induce a concomitant reduction in the levels of C99 and AICD, (FIG. 2C). RNAi-mediated downregulation of ErbB2 resulted in a selective decrease in the C99 signaling, but not Notch signaling, phenocopying CL-387,785-induced effects (FIG. 2D). Our findings strongly favor a model in which ErbB2 modulates the availability of C99 and AICD.

Depletion of ErbB2 Promotes the Autophagic Clearance of C99 and AICD

Figure 3:
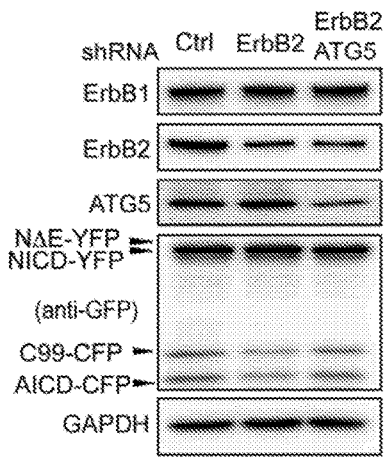
FIG. 3 shows that ErbB2 controls the proteostasis of C99 and AICD through the autophagy-lysosomal pathway, (A) HEK293 cells co-expressing ErbB1, ErbB2, CFP-tagged C99, and YFP-tagged NΔE were infected with lentivirus encoding shRNA targeting LacZ (Ctrl), or ErbB2 for 48 h, followed by treatment with vehicle alone (0.1% DMSO) 10 μM chloroquine (CQ), or 10 mM ammonium chloride at 37° C. for additional 24 h. Clarified lysates containing equivalent amounts of proteins were analyzed by Western blotting. (B, C) HEK293 overexpressing CFP-LC3 cells were infected with lentivirus encoding shRNA targeting LacZ ErbB2, or ErbB2 plus ATG5 for 48 h. The autophagy induction was analyzed by fluorescence confocal microscopy. The number of CFP-LC3 puncta per cell was quantified. The levels of LC3-I, LC3-II, and GAPDH were analyzed by Western blotting. (D, E) HEK293 cells overexpressing ErbB1, ErbB2, CFP-tagged C99, and YFP-tagged NΔE were infected with lentivirus encoding shRNA targeting LacZ (Ctrl), ErbB1, or ErbB2 for 48 h. Infection mixtures were replaced with 2 ml of fresh culture medium, and infected cells were then incubated at 37° C. for an additional 24 h. The levels of LC3-1, LC3-II, and p62 were analyzed by Western blotting and quantified by NIH Image J. Conditional media were harvested and processed for determination of secreted Aβ40 using a colourimetric Aβ40-specific ELISA kit. (F, G) HEK293 cells overexpressing C99-YFP were treated with vehicle (DMSO) or 1 μM CL-387,785 at 37° C. for 24 h and analyzed by Western blotting. Conditional media were harvested for determination of secreted Aβ40. The quantitative data are shown as mean±SD from three independent experiments, and were analyzed by Student's t-tests. * p<0.05.
Figure 3:
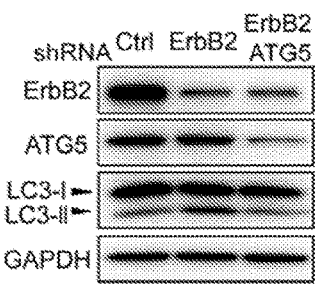
Figure 3:
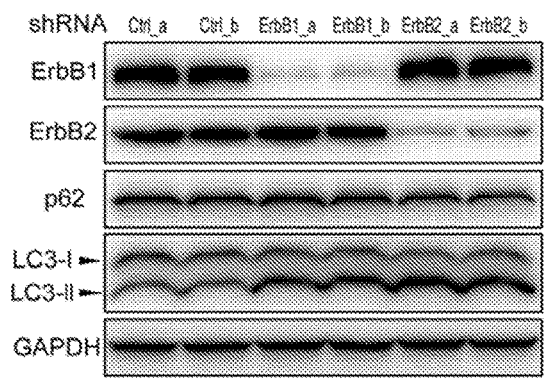
Figure 3:
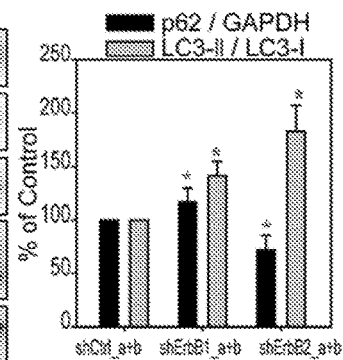
Figure 3:
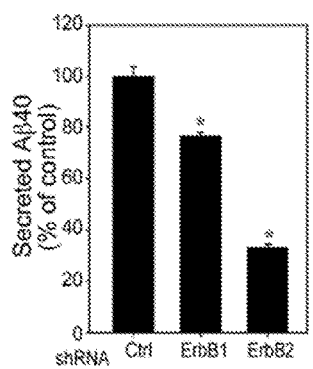
Figure 3:
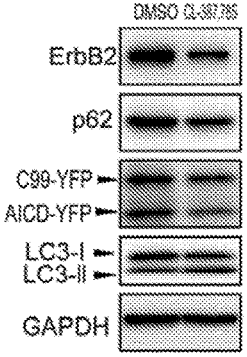
Figure 3:
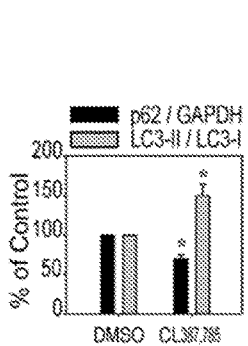
Figure 3:
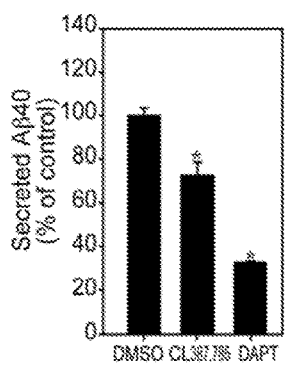

Using HEK293 cells overexpressing ErbB1, ErbB2, CFP-tagged C99, and YFP-tagged NΔE, we demonstrated that the reduction in C99 and AICD elicited by ErbB2 knockdown could be rescued by treatment with either chloroquine or ammonium chloride (FIG. 3A). Using a CFP-LC3-overexpressing HEK293 cell line, we found that ErbB2 knockdown induced a significant accumulation of CFP-LC3 puncta, whereas shErbB2-induced formation of CFP-LC3 puncta was blocked by ATG5 knockdown (FIG. 3B). ErbB2 downregulation increased LC3-II production, which could be reversed by concurrent ATG5 knockdown (FIG. 3C). This suggest a novel role of ErbB2 in modulating autophagy.

To distinguish the potential cross-talk between ErbB2 and ErbB1 in modulating autophagy, we employed a HEK293 cell line that stably overexpressed ErbB1, ErbB2, CFP-tagged C99, and YFP-tagged NΔE to examine the levels of p62 and LC3-I/II in responses to either ErbB1 or ErbB2 knockdown. Our data showed that, while downregulation of ErbB1 resulted in significant accumulation of p62 and an increase in the LC3-II/I ratio, depletion of ErbB2 caused a significant reduction in p62 with a concomitant increase in the LC3-II/I ratio (FIG. 3D), suggesting that inhibition of ErbB2 is sufficient to induce autophagy. Despite the accumulation of C99 and AICD caused by RNAi-mediated downregulation of ErbB1 (FIG. 2C), suppression of ErbB1 can still effectively decrease Aβ40 production (FIG. 3E). More importantly, downregulation of ErbB2 had a much stronger impact than that of ErbB1 on the production of secreted Aβ40 (FIG. 3E). In HEK293 cells that overexpressed C99-YFP, treatments with CL-387,785 led to a significant reduction in p62 and a concurrent increase in LC3-II/LC3-I ratio (FIG. 3F), indicative of autophagy induction. Consistent with the effect induced by ErbB2 knockdown, depletion of ErbB2 by CL-387,785 effectively decreased secreted Aβ40 production (FIG. 3G). These results indicate a novel ErbB2-dependent pathway that governs the autophagic clearance of APP-C99 to modulate Aβ production.

ErbB2 Interferes with the Formation of the Beclin1-Vps34-Vps15 Complex

Figure 4:
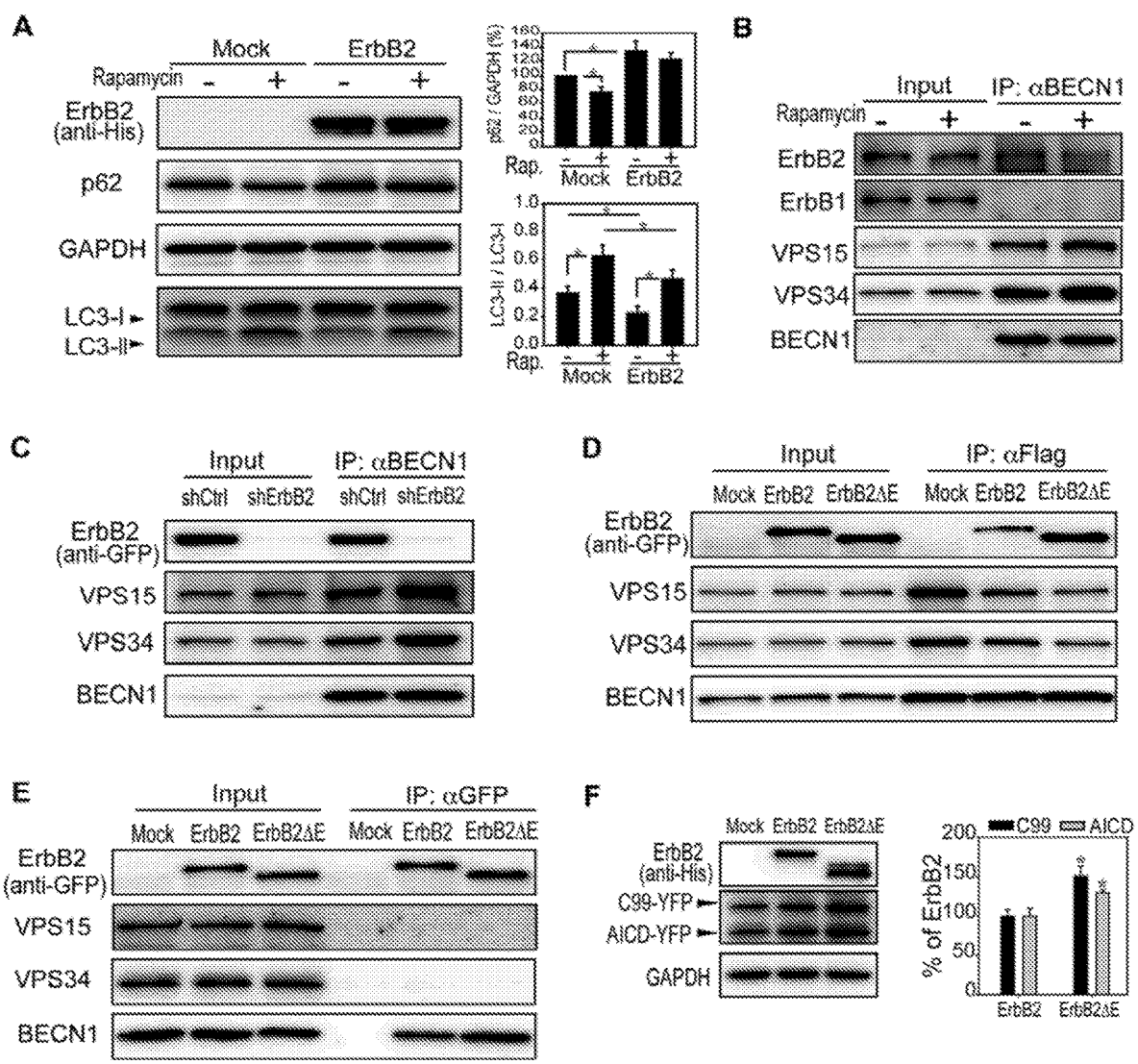
FIG. 4 shows that ErbB2 physically interacts with Beclin-1 and disrupts the formation of the tripartite Beclin-1-Vps34-Vps15 complex. (A) HEK293 cells were infected with control lentivirus (Ctrl) or lentivirus encoding 6×His-tagged ErbB2, and then treated with vehicle (DMSO) or 200 nM rapamycin at 37° C. for 3 h. Clarified lysates containing equal amounts of proteins were analyzed by Western blotting and quantified by Image J. The quantitative data are shown as the mean±SD from three independent experiments, and were analyzed by Student's t-tests. * p<0.05. (B) HEK293 cells were treated with vehicle (DMSO) or 200 nM rapamycin at 37° C. for 3 h. Clarified lysates were immunoprecipitated with anti-Beclin-1 antibody (αBECN1). Immobilized proteins were analyzed by Western blotting with anti-ErbB1, anti-ErbB2, anti-Vps15, anti-Vps34, and anti-Beclin-1 antibodies. (C) HEK293 cells overexpressing YFP-tagged ErbB2 were infected with lentivirus encoding shRNA targeting LacZ (Ctrl) or ErbB2 (shErbB2) at 37° C. for 72 h. Clarified lysates with equal amounts of proteins were subject to immunoprecipitation with anti-Beclin-1 antibody (αBECN1). Immobilized proteins were analyzed by Western blotting with anti-ErbB2, anti-Vps15, anti-Vps34, and anti-Beclin-1 antibodies. (D, E) HEK293 cells expressing FLAG-Beclin-1 were infected with control lentivirus (Ctrl) or virus encoding either YFP-tagged ErbB2 or YFP-tagged ErbB2-ΔE. Clarified lysates were then immunoprecipitated with anti-FLAG antibody (αFlag) (D) anti-GFP (E) antibody. (F) HEK293 cells expressing C99-YFP were infected with control lentivirus (Ctrl) or lentivirus encoding either His-tagged ErbB2 or His-tagged ErbB2ΔE at 37° C. for 72 h, and were analyzed by Western blotting.

We determined whether and how the binding of ErbB2 to Beclin-1 may mediate the regulation of autophagic flux to control the degradation of C99. Consistent with the finding that ErbB2 acts as a negative regulator of autophagy, overexpression of ErbB2 in HEK293 cells caused p62 accumulation and decreased autophagic flux (LC3-II/I ratio) (FIG. 4A). When treated with rapamycin, ErbB2 overexpressing-HEK293 cells exhibited an inefficient p62 degradation and a lower LC3-II/I ratio as compared to the rapamycin-treated mock-transfected control (FIG. 4A). This suggest that overexpression of ErbB2 can withstand the rapamycin-induced autophagy initiation. Endogenous ErbB2 in HEK293 cells associated with Beclin-1 at basal state as well as at rapamycin-treated state, while there was no detectable interaction between EGFR and Beclin-1 in the presence or absence of rapamycin (FIG. 4B). ErbB2 knockdown can strengthen the interaction between Beclin-1 and the Vps34-Vps15 complex (FIG. 4C), suggesting that downregulation of ErbB2 can free up Beclin-1 and enhance the binding of Beclin-1 with VPS15/VPS34 to augment autophagic flux. In HEK293 cells overexpressing FLAG-tagged Beclin-1, overexpression of constitutively active ErbB2ΔE resulted in even greater attenuation in the binding of Beclin-1 to the Vps34-Vps15 complex than wtErbB2 did (FIG. 4D). The ErbB2-Beclin-1 complex did not contain Vps34-Vps15 (FIG. 4E), suggesting that overexpression of ErbB2 can disrupt the assembly of autophagy initiation complexes. Overexpression of ErbB2ΔE resulted in a greater accumulation of C99 and AICD than wtErbB2 did C99-YFP-expressing HEK293 cells (FIG. 4E). Using immunfluorescence confocal microscopy, we demonstrated that wtErbB2 and mutant ErbB2ΔE are co-localized with Beclin-1 at basal state. The data suggest that ErbB2 actively governs autophagic flux through limiting the availability of Beclin-1 to the Vps34-Vps15 complex.

Monomeric and Kinase-Dead ErbB2 can Interact will Beclin-1

Figure 5:
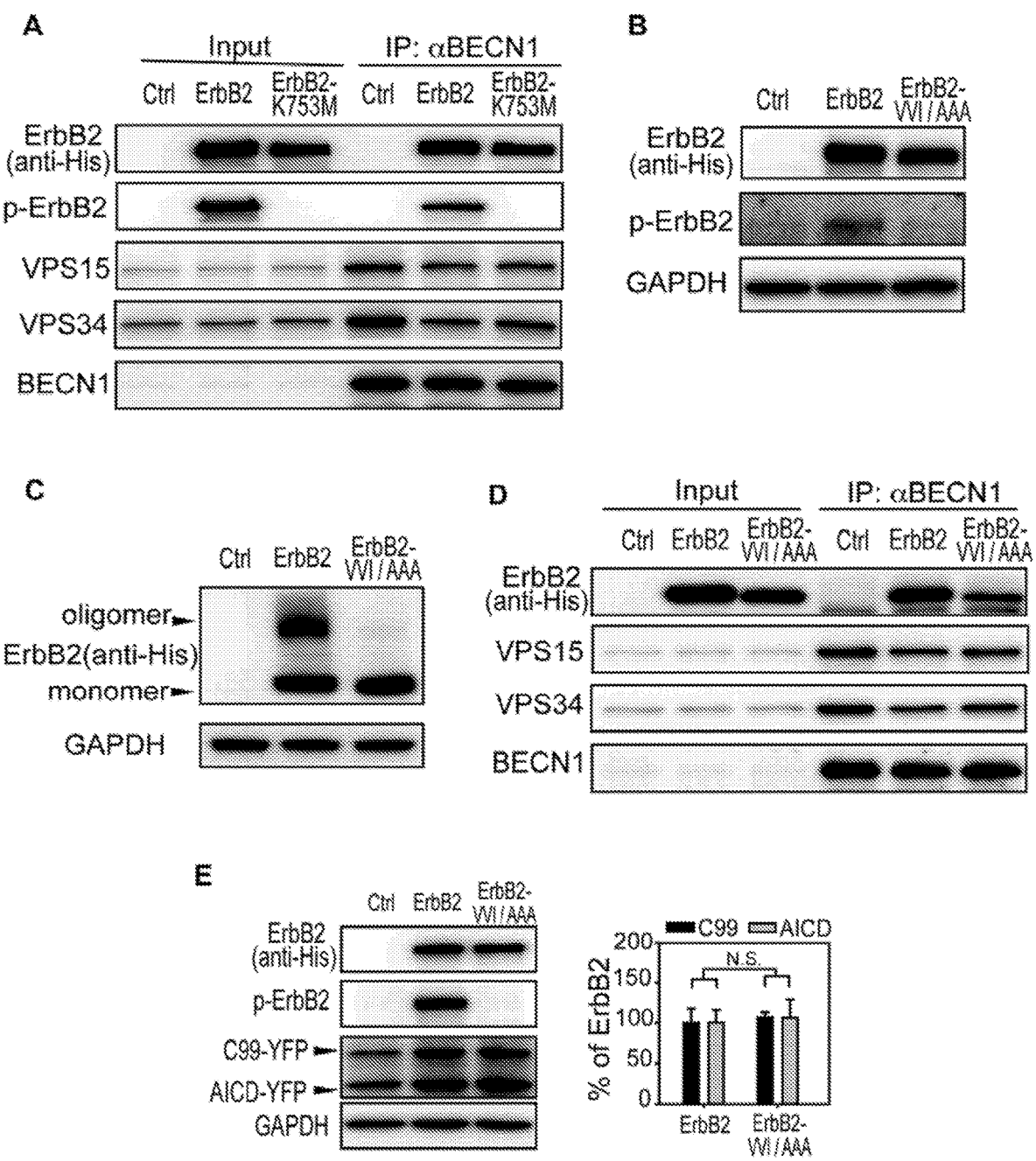
FIG. 5 shows that monomeric and oligomeric ErbB2 binds to Beclin-1 independent of its kinase activity. (A) HEK293 cells were infected with control lentivirus (Ctrl) or lentivirus encoding either His-tagged ErbB2 or His-tagged ErbB2-K753M, and were then immunoprecipitated with anti-Beclin-1 (αBECN1). (B) CHO-K1 cells were infected with control lentivirus (Ctrl) or lentivirus encoding either His-tagged ErbB2 or His-tagged ErbB2-VVI/AAA(966-968). Clarified cell lysates were analyzed by Western blotting using anti-His (for ErbB2), anti-phospho-HER2/ErbB2 (Tyr1248), and anti-GAPDH. (C) Clarified lysates derived from infected CHO-K1 cells expressing ErbB2 car ErbB2-VVI/AAA were incubated with a crosslinker BS3 (bis (sulfosuccinimidyl)suberate) (1 mM, Thermo Fisher Scientific) at room temperature for 2 h, and were then analyzed by Western blotting with anti-His antibody (for ErbB2). These results confirmed that the mutant ErbB2 (ErbB2-VVI/AAA) exists as a monomeric form and lacks kinase activity. (D) CHO-K1 cells were infected with control lentivirus (Ctrl) or lentivirus encoding either His-tagged ErbB2 or His-tagged ErbB2-VVI/AAA (966-968), and were then immunoprecipitated with anti-Beclin-1 (αBECN1), followed by Western blotting with antibodies against Beclin-1, Vps34, Vps15, and His tag. (E) HEK293 cells overexpressing C99-YFP were infected with control lentivirus (Ctrl) or lentivirus encoding either His-tagged ErbB2 or His-tagged ErbB2-VVI/AAA at 37° C. for 72 h, and were analyzed by Western blotting. Clarified lysates containing equal amounts of proteins were analyzed by Western blotting and quantified by Image J. The quantitative data are shown as the mean±SD from three independent experiments, and were analyzed by Student's t-tests. * p<0.05.

To determine whether the ErbB2 kinase activity is required for its role in the regulation of autophagic flux, we examined the interaction between Berlin-1 and the Vps34-Vps14 complex in response to the overexpression of wild-type ErbB2 or a kinase-dead mutant (KD) ErbB2 (K753M). HEK293 cells overexpressing wild-type ErbB2 or KD-ErbB2 exhibited a comparable binding with Beclin-1, suggesting that binding of ErbB2 with Berlin-1 is kinase-independent (FIG. 5A). To further verify the physical interaction between ErbB2 and Beclin-1 and to rule out the potential involvement of other ErbB isoforms, we employed CHO-K1 cells that do not express ErbB1, ErbB3, and ErbB4 for further studies. Overexpression of wtErbB2 or a kinase-dead and monomeric mutant ErbB2 [ErbB2-VVI/AAA(966-968), in CHO-K1 cells was performed, and their interaction with Beclin-1 was analyzed by co-immunoprecipitation using anti-Beclin-1 antibody. We found that monomeric mutant ErbB2-VVI/AAA binds to Beclin-1 and attenuates Beclin-1's association with Vps34-Vps15 complex as effectively as wtErbB2 does (FIG. 5B-D). Consistently, overexpression of ErbB2-VVI/AAA in C99-YFP-expressing HEK293 cells caused a significant accumulation of C99 and AICD comparable to what wtErbB2 did (FIG. 5E). This suggest that monomeric ErbB2 is sufficient to bind Beclin-1 and regulate autophagic flux in a kinase independent manner.

Inhibition of ErbB2 Significantly Alleviates the Production of C99 and AICD in Neuroblastoma Cells and a Zebrafish Model of AD To substantiate the critical role of ErbB2 in the homeostasis of APP processing and Aβ production, we examined the level of secreted Aβ40 in conditioned media derived from cells treated with CL-387,785 or infected with lentiviral vectors encoding either ErbB1- or ErbB2-targeting shRNAs. Chemical depletion of ErbB2 by CL-387,785 significantly reduced the levels of C99, AICD, and secreted Aβ40 in IMR32 neuroblastoma cells overexpressing C99-YFP (FIG. 6A-B). These findings were further confirmed by the data that RNAi-mediated downregulation of ErbB2 (shErbB2) significantly reduced the levels of C99, AICD, and secreted Aβ40 in C99-YFP-expressing IMR32 cells, while ErbB1 knockdown (shErbB1) induced a slight increase in the accumulation of C99 and AICD but a marginal reduction in Aβ40 (FIG. 6C-D).

To determine whether ErbB2 mediates selective modulation of the proteostasis of C99 in vitro, we generated a zebrafish model of AD, in which embryos express GFP-tagged C99 (FIG. 6E). Using this C99-expressing zebrafish model of AD, we found that embryos treated with CL-387,785 exhibited a concomitant clearance of C99 and AICD (FIG. 6F). Unlike the severe developmental defects in DART-treated zebrafish embryos due to the concomitant blockade of Notch signaling by pan-inhibition of γ-secretase, all but one CL-387,785-treated embryos exhibited wild-type trunks and tails with normal pigmentation (FIG. 6G). This suggest that preferential depletion of ErbB2 by CL-387,385 could be developed as a novel therapeutic approach for AD with minimal side effects.

Inhibition of ErbB2 Significantly Alleviates the Production of Aβ and Renders Cognitive Improvement in APP/PS1 Transgenic Mice To correlate the increased level of ErbB2 with defective autophagy in AD brain, we validated that lysates derived from hippocampus regions of AD patients contain a significantly increased accumulation of autophagic cargo receptor p62 as compared to age-matched controls, suggesting that ErbB2-triggered autophagic deficiency is tightly associated with AD pathogenesis FIG. 1). We further confirmed the biological efficacy of CL-387,785 on a murine model of AD. The dosing regimen of CL-387,785 (5 mg/kg/d) did not induce any significant adverse effect on those APPswe/PS1ΔE9 double transgenic mice, as evidenced by no significant difference in body weight of animals treated with CL-387,785 or vehicle alone. Treated APPswe/PS1ΔE9 transgenic mice along with wild-type littermates were subject to spatial learning and memory test by Morris water maze after 11 days of daily dosing on a daily basis. We found that APPswe/PS1ΔE9 transgenic mice administered with CL-387,785 exhibited a significantly enhanced spatial learning after 16 days of daily dosing (FIG. 7A). After 3 weeks of daily dosing, AD mice treated with CL-387,785 exhibited a dramatic cognitive improvement as compared to vehicle-treated AD mice on the probe test with invisible platform (FIG. 7B). Western blotting analysis of the brain homogenates of these APPswe/PS1ΔE9 transgenic mice further revealed that treatments with CL-387,785 induced a significant reduction in the levels of ErbB2, p62, and APP-CTF, concomitant with an increase in the ratio of LC3-II to LC3-I and a steady level of total APP (FIG. 7C-D). Using co-immunoprecipitation, we verified that treatments with CL-387,785 in APPswe/PS1ΔE9 mice inhibited the phosphorylation of EGFR(ErbB1), and drastically suppressed the interaction between ErbB2 with Beclin-1 (FIG. 7E), consistent with its effect on restoring autophagic flux. Most importantly, APPswe/PS1ΔE9 mice treated with CL-387, 785 exhibited an approximately 40% reduction in the levels of Aβ40 and Aβ42 in brain (FIG. 7F). Our findings unveil a new function of ErbB2 in the regulation of autophagic flux that contributes to the proteostasis of APP-C99, and thereby identify a novel therapeutic target for the development of anti-AD drugs with minimal side effects.

The findings suggest that monomeric ErbB2 can cause the disassembly of the Beclin1-Vps34-Vps15 complex, and thereby inhibit the initiation of autophagy. Downregulation of ErbB2 by CL-387,785 or shErbB2 rescues the formation of the Beclin1-Vps34-Vps15 complex. Reduction of ErbB2 not only decreases C99 and AICD, but also concomitantly attenuates Aβ production without significantly affecting the physiological function of γ-secretase (unchanged Notch signaling). At a resting state in the absence of EGF signal, ErbB1 does not interact with Beclin-1 and plays no significant role in the regulation of autophagy initiation, which might be the reason that ErbB1 kinase inhibition cannot promote the clearance of Aβ (FIGS. 4B and 7E).

Figure 7:
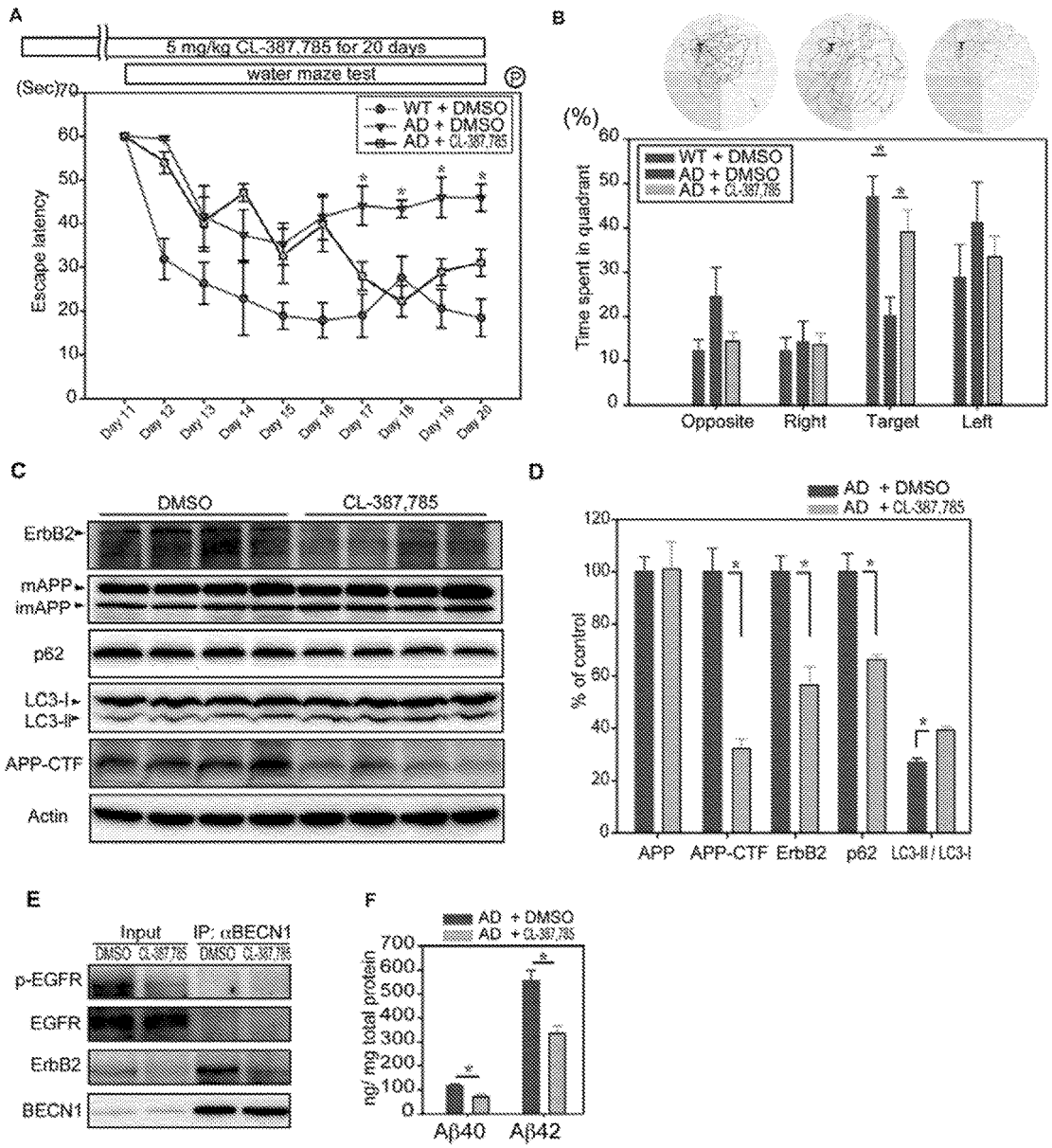
FIG. 7 shows that Inhibition of ErbB2 by CL-387,785 significantly improve learning and memory in APP/PS1 transgenic mice. (A) Fifteen-month-old mice were given daily oral doses of vehicle (DMSO) or 5 mg/kg CL-387,785 for 20 days. Escape latency from day 11 to 20 are shown as means±SEM, and were analyzed by two-way ANOVA (* p<0.5), n=4. P, probe test. (B) Tracking maps and time spent in each of the four quadrants for 90 sec on day 21. Data are shown as the means±SEM, and were analyzed by two-way ANOVA (* p<0.5). T indicates the target quadrant where the invisible platform is located. (C) Western blotting and (D) quantitative results of the right brains of mice after drug treatment. The quantitative data are shown as the mean±SEM and were analyzed by Student's t-tests. * p<0.5. (E) Homogenized brain lysates from DMSO or CL-387,785 treatment group were mixed and immunoprecipitated with anti-BECN1. (F) Homogenized brain lysates were dissolved in 5M guanidine HCl and processed for determination of Aβ40 and Aβ42 using colorimetric Aβ40- and Aβ42-specific ELISA kits. Data were normalized to total protein concentration and analyzed by Student's t-tests (mean±SEM, * p<0.5).

ErbB2 in monomeric form is sufficient to dictate the autophagy-mediated clearance of APP C99 and selective downregulation of ErbB2 can reduce Aβ production without affecting the processing of Notch, a physiological substrate of γ-secretase. Overexpression of a kinase-dead ErbB2 monomer or a constitutively active ErbB2 can induce dissociation of Beclin-1 from Vps34-Vps15-containing autophagy initiation complex and thus prevent the autophagic clearance of APP-C99, resulting in accumulation of APP-C99 and AICD. Both the chemical inhibition of ErbB2 by CL-387,785 and RNAi-mediated genetic depletion of ErbB2 can rescue the formation of Beclin-1-Vps34-Vps15 autophagy initiation complex to propagate the autophagic clearance of APP-C99, leading to a reduction in Aβ and cognitive function improvement (FIG. 7). The data also demonstrates that the homeostasis of APP processing and Aβ production can be selectively manipulated without compromising the physiological functions of other γ-secretase substrates, such as Notch.

ErbB2 plays a more prominent role in hindering autophagy initiation than the EGFR/ErbB1 does, since monomeric ErbB2 can effectively disassemble Beclin-1-Vps34-Vps15 complex. The study suggests a novel molecular basis by which ErbB2 may act as a scaffold of Beclin-1 to keep autophagy activity at a resting state in the absence of EGF signal. These findings favor a model in which ErbB2 could work as the gatekeeper of autophagic flux. Our data also suggest that ErbB2 might play a more prominent role than EGFR/ErbB1 does in the progression of AD, since EGFR/ErbB1 expression is not significantly changed in AD brain.

We have identified a novel function of oncogenic receptor tyrosine kinase ErbB2 at its monomeric form, and provide proof-of-concept evidence suggesting that the increased levels of ErbB2 in hippocampus could potentially be established as a diagnostic marker of sporadic AD. These findings also favor a model in which ErbB2 serve as the negative regulator of autophagy initiation, and implicate ErbB2 as an alternative therapeutic target for novel AD therapies.

The foregoing description of the exemplary embodiments of the invention has been presented only for the purposes of illustration and description and is not intended to be exhaustive or to limit the invention to the precise forms disclosed. Many modifications and variations are possible in light of the above teaching. All references cited in this specification are incorporated herein by reference in their entireties and to the same extent as if each reference was individually incorporated by reference.

What is claimed is:

1. A method for enhancing spatial learning and memory, and/or for improving cognitive function, in a subject in need thereof, comprising:
   administering to the subject in need thereof a therapeutically effective amount of an ErbB2 inhibitor to enhance the spatial learning and memory, and/or improve the cognitive function, wherein the subject in need thereof has ErbB2-associated Alzheimer's disease.

2. The method of claim 1, wherein the subject exhibits one of the following characteristics:
   (i) loss of memory;
   (ii) loss of spatial memory and learning ability; and
   (iii) over-expression and or a high level of ErbB2 in the hippocampus of the brain.

3. The method of claim 1, wherein the subject is afflicted with sporadic Alzheimer's disease.

4. The method of claim 1, wherein the ErbB2 inhibitor is selected from the group consisting of CL-387785, ErbB2-targeting short hairpin RNAs (shRNAs), and ErbB2-targeting small interfering RNAs (siRNAs).

5. The method of claim 1, wherein the ErbB2 inhibitor exhibits one of the following characteristics:
   (i) having a specific binding affinity to ErbB2 monomer and having no effect on γ-secretase activity; and
   (ii) having no effect on extracellular domain-truncated Notch, Notch intracellular domain levels, and Notch signaling.

6. The method of claim 1, wherein the ErbB2 inhibitor is formulated for a dosing regimen of once daily for more than 2 weeks, or for no less than 3 weeks.

7. The method of claim 1, wherein the ErbB2 inhibitor is formulated for a dosing regimen of once daily at a human equivalent dose of about 5 mg/Kg×$(0.040$ Kg/weight of human in Kg$)^{0.33}$ or more.

8. The method of claim 1, wherein the subject is a mammal.

9. The method of claim 1, wherein the subject is afflicted with Aβ-induced neurotoxicities.

10. The method of claim 1, wherein the ErbB2 inhibitor exhibits the activity of promoting ErbB2-regulated autophagic degradation or clearance of amyloid precursor protein C-terminal fragment (APP-C99) and APP intracellular domain (AICD), and/or alleviating production of Aβ40 and Aβ42 in the subject in need thereof.

11. The method of claim 1, wherein the ErbB2 inhibitor exhibits the activity of rescuing ErbB2-mediated inhibition of autophagic flux, and/or restoring the formation of Beclin-1-Vps34-Vps15 autophagy initiation complex in the subject in need thereof.

12. A method for enhancing spatial learning and memory in a patient with ErbB2-associated Alzheimer's disease in need thereof, comprising:
    administering a therapeutically effective amount of CL-387785 to the patient with the ErbB2-associated Alzheimer's disease in need thereof to enhance the spatial learning and memory.

* * * * *